United States Patent [19]

Ely

[11] 4,022,882
[45] May 10, 1977

[54] GERMICIDAL SOLUTIONS AND METHODS FOR PRESERVING AND PURIFYING MILK, OTHER BEVERAGES, FOODS, WATER AND SEWAGE EFFLUENT

[75] Inventor: Hollis Ely, Bourbonnaise, Ill.

[73] Assignees: Joan A. Hammel, Joliet, Ill.; Richard J. Hammel, Brookfield, Wis.; part interest to each

[22] Filed: Jan. 15, 1976

[21] Appl. No.: 649,343

Related U.S. Application Data

[63] Continuation-in-part of Ser. No. 485,526, July 3, 1974, which is a continuation-in-part of Ser. No. 285,045, Aug. 30, 1972, which is a continuation-in-part of Ser. Nos. 849,143, Aug. 11, 1969, and Ser. No. 262,707, June 14, 1972, abandoned.

[52] U.S. Cl. .............................. 424/80; 426/260; 426/532; 426/580; 426/590; 426/599; 426/330.2; 426/330.3; 210/62; 252/401

[51] Int. Cl.$^2$ ........................................ A23L 2/18

[58] Field of Search ............. 424/80, 150; 210/62; 252/401; 426/253, 260, 321, 334, 335, 654, 151, 330, 262, 580, 599, 330.2, 330.3

[56] References Cited

UNITED STATES PATENTS

| | | | |
|---|---|---|---|
| 2,382,193 | 8/1945 | Whitmoyer | 426/321 |
| 2,739,922 | 3/1956 | Shelanski | 426/70 |
| 3,028,300 | 3/1962 | Cantor | 167/17 |
| 3,620,773 | 11/1971 | Gabriel | 426/335 |

OTHER PUBLICATIONS

The Condensed Chemical Dictionary – Howley, 8th Ed., Van Nortrand, N.Y., p. 451.

*Primary Examiner*—Hiram H. Bernstein
*Attorney, Agent, or Firm*—Burmeister, York, Palmatier, Hamby & Jones

[57] ABSTRACT

Milk or other beverages or foods may be preserved by adding thereto a minor amount of an aqueous germicidal solution of elemental iodine, hydrazine as hydrazine hydrate, and an organic carrier, such as polyvinyl pyrrolidone, with sufficient water to dissolve the other constituents. Such beverages include fruit juices and soft drinks. The germicidal solution may also be employed advantageously for purifying water to be used for drinking or swimming pool purposes, and also for purifying sewage effluent. The polyvinyl pyrrolidone largely overcomes the odor and taste of the iodine in the solution, while the hydrazine completely overcomes the iodine color. Nevertheless, the germicidal effectiveness of the solution is maintained. Sufficient hydrazine is employed to cause the iodine to be dissolved in the water and to remove the iodine color. A modified aqueous solution containing only elemental iodine and hydrazine as hydrazine hydrate may also be employed for the same purposes. The germicidal solutions can also be employed very advantageously as sanitizing and cleansing agents, which are effective, yet non-toxic.

2 Claims, No Drawings

GERMICIDAL SOLUTIONS AND METHODS FOR PRESERVING AND PURIFYING MILK, OTHER BEVERAGES, FOODS, WATER AND SEWAGE EFFLUENT

This application is a continuation-in-part of my copending application Ser. No. 485,526, filed July 3, 1974, which was a continuation-in-part of my application Ser. No. 285,045, filed Aug. 30, 1972 which was a continuation-in-part of my earlier applications Ser. No. 849,143, filed Aug. 11, 1969, and Ser. No. 262,707, filed June 14, 1972 and now abandoned.

This invention relates to the preservation of milk, fruit juices, soft drinks, other beverages and foods subject to spoilage, and also to germicidal solutions which are useful for such preservation. The invention also relates to the purification of liquids by the destruction of pathogenci bacteria and other organisms therein by the addition of germicidal solutions thereto. Such liquids include water for drinking or swimming pool purposes, and also sewage effluent.

Heretofore, pasteurization and refrigeration have been relied upon to preserve milk, other beverages and foods. However, both of these procedures are expensive and not entirely effective. Moreover, there are many situations in which it is impossible or extremely difficult to refrigerate milk, other beverages and foods. Such situations include camping trips and military operations.

In the past, the principal method of purifying water and sewage effluent has been to add chlorine or compounds which release chlorine in the water. However, chlorine is not entirely effective and its taste, odor and bleaching effect are often objectionable.

One principal object of the present invention is to provide chemical methods of preserving milk, other beverages and foods by the addition of germicidal solution thereto.

A further object is to provide new and improved methods of purifying liquids, such as water and sewage effluent, by the addition of germicidal solutions thereto.

Another object is to provide for such chemical preservation without problems of toxicity or detriment to the taste, odor or apperance of the milk, other beverage or food. Likewise, it is an object of the invention to provide for such purification of liquids such as water and sewage effluent without imparting any appreciable taste, odor or color to such liquids.

A further object is to provide inexpensive chemical preservatives and purifying solutions which are highly effective and stable, yet can be manufactured and used without difficulty.

In accordance with the present invention, milk, fruit juices, soft drinks, other beverages and foods may be preserved by adding thereto a minor amount of an aqueous solution consisting essentially of elemental iodine, hydrzine, preferably in the form of hydrazine hydrate, and an organic carrier, preferably polyvinyl pyrrolidone with sufficient water to dissolve the constituents. The method is also applicable to milk derivatives and substitutes therefor. Either cold or warm water can be used.

The hydrazine assists in dissolving the iodine while also removing the reddish iodine color, so that the solution is colorless. The organic carrier renders the iodine and hydrazine substantially non-toxic while also preventing the iodine and hydrazine from imparting any appreciable taste or odor to the milk or other beverage or food. The organic carrier largely neutralizes the taste and odor of the iodine.

The organic carrier may be derived from the polyvinyl family, and, as indicated, preferably comprises polyvinyl pyrrolidone. Sufficient hydrazine hydrate is employed to cause the iodine to dissolve in the water, and to decolorize the iodine. A sufficient quantity of polyvinyl pyrrolidone is utilized to overcome the taste and odor of the iodine.

While the solution is non-toxic, it has very substantial germicidal ability so that it effectively combats pathogenic bacteria and other organisms, even when only a minor amount of the solution is employed in milk, fruit juices, soft drinks and other beverages and foods which are subject to spoilage.

The germicidal solution may also be used very advantageously for purifying drinking water, or water which is to be used in a swimming pool. The solution does not impart any noticeable taste, odor or color to the water.

The solution may also be advantageously employed as a germicidal agent to pruify sewage effluent. While the solution combats microorganisms over an extended period, it is non-toxic to fish.

Preferably, the constituents of the preservative solution are substantially in the following proportions by weight: 100 parts of elemental iodine, 40–60 parts of 64% hydrazine hydrate solution in water, and 20–100 parts of the organic carrier in the form of polyvinyl pyrrolidone. The K factor of the polyvinyl pyrrolidone is preferably about 30 to 90. Intermediate values and other K values may also be employed.

The germicidal solution with these constituents is colorless and has only a very slight taste and odor. However, when the germicidal solution is used in minor yet effective amounts in milk, other beverages, and foods, it does not impart any appreciable taste or odor to the beverage.

For convenience, the hydrazine is preferably supplied by using a aqueous solution of hydrazine hydrate. Hydrazine itself can be used, but it reacts violently with water to form hydrazine hydrate. Only enough hydrazine need be added to remove the iodine color from the solution. The amount of hydrazine to be added depends upon the amount of elemental iodine in the solution. For each gram of elemental iodine, it has been found that the iodine color can be removed by adding approximately one-half milliliter of a 64% aqueous solution of hydrazine hydrate. The decolorized solution retains its germicidal strength and may be employed to preserve milk and other beverages and foods for long periods of time.

A highly advantageous modified germicidal solution may also be employed utilizing only hydrazine and elemental iodine in the water. The hydrazine causes the iodine to be easily dissolved in the water, and also overcomes the color of the iodine. The mixture has only a slight taste and odor which are usually not objectionable. It is preferred to use only enough hydrazine to prevent the development of the iodine color in the water. This germicidal solution is colorless and almost odorless and tasteless, yet has a great germicidal strength. In may be employed very advantageously for preserving milk, and also fruit juices, soft drinks and other beverages and foods subject to spoilage. The solution may also be employed very effectively to purify water and sewage effluent. The solution does not impart any color, or any appreciable odor or taste to drinking water and is non-toxic. The alternative solution is less costly because the polyvinyl pyrrolidone is not used.

Various examples will serve to illustrate the practice of the invention.

EXAMPLE I

To make one gallon of a germicidal solution, 50 Grams of polyvinyl pyrrolidone (PVP) were dissolved in 3/4 gallon of water by adding the PVP to the water with adequate agitation. To this solution, 200 grams of elemental iodine were added, plus 375 milliliters of an 18% hydrazine hydrate solution in water. It is preferred to add the hydrazine hydrate solution slowly, 100 milliliters at a time, with adequate agitation so that all of the constituents will be fully dissolved in the water. Enough water may then be added to the solution to make one gallon. No other ingredient was used.

The amount of water in the solution is not critical. It is only necessary to use sufficient water to dissolve the other consitituents, but it may be more convenient to dilute the solution with additional water, if desired.

Either distilled water or tap water may be employed in the solution. If the tap water is fairly hard, it is preferred to deionize the water before using it in the solution. If the tap water contains any appreciable amount of suspended solids, it is preferred to filter the water, or otherwise remove the suspended material.

Minor amounts of the germicidal solution may be added as a preservative to beverages and foods which are subject to spoilage. Thus, small amounts of the germicidal solution may be added as a preservative to such beverages as milk, milk, derivative beverages, fruit juices, fruit juice derivative beverages, soft drinks and the like.

Various concentrations of the germicidal solution may be employed as a preservative in beverages and foods, depending on various factors, such as the nature of the particular beverage or food, the temperature and other conditions under which it is to be preserved, and the initial concentration of microorganisms in the food or beverage. It has been found that a concentration of 5 parts per thousand is effective and suitable as a preservative in most cases. Thus, for example, 5 milliliters of the germicidal solutions may be added as preservative to milk, fruit juices, soft drinks, and other beverages. At this concentration, the preservative solution kills both Gram positive and Gram negative organisms.

At a concentration of 5 parts per thousand, the germicidal solution has a dramatic preservative action when added to raw milk. It has been observed that raw milk will ordinarily turn sour within 8 to 11 hours at 95° (F). When the germicidal solution is added to raw milk at a concentration of 5 parts per thousand, it has been found that the raw milk will stay sweet and palatable at this temperature for 120 hours or more.

When the same concentration of the germicidal solution is added as a preservative to pasteurized milk, it has been found that the palatable shelf life of the milk is as much as the times the normal expectancy.

Small concentrations of the germicidal solution may be employed as a preservative in fruit juices in place of pasteurization, to preserve the initial quality and taste, while also holding the vitamin content intact.

Small concentrations of the germicidal solution may be used as a preservative in foods which are subject to spoilage by organisms such as Salmonella or Clostridium Botulinum. The preservative solution effectively prevents spoilage by these organisms for long periods of time. Thus, for example, the germicidal solution is valuable as a preservative for cranberries, which have been subject to Salmonella spoilage, and mushrooms, which are subject to Botulism development.

The germicidal solution is also effective and valuable as an additive in animal feeding, to protect the animals from microorganisms. For example, small concentrations of the germicidal solution may be used as an additive in poultry feed, as a substitute for the arsenic compounds which have been employed in the past. Eliminating the arsenic compounds eliminates the arsenic carry-over to the eggs and meat derived from the poultry, so that the poisonous action of the arsenic to humans is entirely avoided. The germicidal solution of the present invention has no toxic effect or carry-over.

The germicidal solution has several other advantages. First, it does not contain any potassium or sodium. Second, the germicidal solution is clear and completely stable. Third, its taste is very slight and not objectionable. No appreciable taste or odor is imparted to beverages or foods, when the germicidal solution is employed in small yet effective concentrations. Fourth, the preparation of the germicidal solution is simple and easy. Such preparation involves only mixing, the simplest of all chemical processes. No heat is used or evolved from the process. Fifth, various tests can be employed to check the concentration of the iodine and the other constituents.

In this germicidal solution, the oidine is the main bacteria killer. With the cooperative action of the hydrazine and PVP, a small amount of the solution does a big job, and also an inexpensive job, when compared with present methods.

Hydrazine hydrate is often supplied commercially as a 64% solution. Instead of using 375 milliliters of the 18% hydrazine hydrate solution in preparing the germicidal solution, an equivalent amount of a 64% solution may be employed. Such equivalent amount is approximately 105.5 milliliters. Enough of the hydrazine hydrate should preferably be used to eliminate the iodine color from the germicidal solution. It is wasteful and unnecessary to use excess hydrazine hydrate. Moreover, any excess hydrazine hydrate will tend to impart a taste to the germicidal solution.

It may be helpful to restate the proportions of the germicidal solution on the bases of 100 of elemental iodine On this basis, the proportions of Example I are reduced to 100 grams of elemental iodine, 25 grams of PVP, and 187.5 milliliters of the 18% solution of hydrazine hydrate, plus enough water to make one-half gallon of the germicidal solution. This is approximately 2 liters. The equivalent amount of the 64% hydrazine hydrate solution is approximately 52.7 milliliters. It will be noted that each gram of elemental iodine requires approximately ½ milliliter of the 64% hydrazine hydrate solution.

The K factor of the polyvinyl pyrrolidone, indicating the extent of its polymerization, may be varied over a wide range. Using polyvinyl pyrrolidone having an increased K factor tends to produce a germicidal solution which is improved in that it is longer lating so that the milk or other beverage, or food to which the germicidal solution is added, will be preserved for a longer period of time.

When polyvinyl pyrrolidone having a high K factor is used, it tends to produce a gel in the solution when it is first mixed. However, the solution clears and the gel disappears after the solution has been allowed to stand overnight or for an extended period.

It has been found that a highly useful and effective germicidal solution may be produced by dissolving hydrazine and iodine in water, without using PVP. The hydrazine makes it possible to dissolve the iodine without the use of an iodide in the solution. Moreover, the hydrazine decolorizes the iodine and renders it almost tasteless and odorless. Only enough hydrazine need be used to decolorize the iodine. Any excess hydrazine is wasteful and tends to impart a taste to the solution. The iodine-hydrazine solution is an effective germicide and is highly effective as a preservative for milk and other beverages and foods.

The following example will illustrate the use of an iodine-hydrazine solution.

EXAMPLE II

A germicidal, preservative solution was prepared by adding 4 milliliters of a 64% aqueous solution of hydrazine hydrate to 75 milliliters of water. The solution was completed by dissolving approximately 8 grams of elemental iodine in the solution, which was colorless, and almost tasteless and odorless. No other ingredient was used. If too much iodine is added, the reddish iodine color will appear. Distilled water is not a necessity. Ordinary tap water is adequate.

In one test, 5 drops of the iodine-hydrazine solution were added to 20 milliliters of milk which then remained sweet and drinkable at room temperature (75°-80°) for 98 hours. The solution did not affect the taste, odor or appearance of the milk.

Hydrazine itself can be used instead of hydrazine hydrate, but this is generally undesirable because the hydrazine reacts violently with the water to which it is added. The hydrazine is converted to hydrazine hydrate in the water. It is generally more desirable to obtain the hydrazine and use it in the form of an aqueous solution of hydrazine hydrate.

It will be helpful to convert the proportions of Example II to the basis of 100 parts of iodine. This conversion results in the following proportion: Add 50 milliliters of a 64% aqueous solution of hydrazine hydrate to 937.5 milliliters of water, and dissolve 100 grams of elemental iodine in the resulting dilute hydrazine solution.

The germicidal solutions of the present invention may be employed very effectively to preserve all fluid and semi-fluid forms of milk and milk derivatives, such as raw milk, pasteurized milk, homogenized milk, yogurt, all forms of cream, such as coffee cream and whipping cream, sour cream, ice cream, ice milk, cottage cheese, and whipped cream products. Moreover, the germicidal solutions may be employed to preserve various substitutes for milk and its derivatives, such as various whipped cream substitutes.

Accordingly, the term milk should be understood as including these various milk derivatives and substitutes. The present invention is also applicable to the preservation of a wide variety of semi-fluid food products and other food products with which the germicidal solutions can be mixed. When the preservative solutions of the present invention are used, milk and its various derivatives and substitutes will keep for many days without refrigeration, and will keep for many weeks with refrigeration. The same is true of various other foods and beverages which are subject to spoilage.

The germicidal solutions of this invention may be employed to preserve cider, other fruit juices, soft drinks and other beverages subject to spoilage, in the same manner as in the case of milk.

The germicidal, preservative solutions of these examples destroy or prevent the growth of bacteria which cause milk to go sour. Pathogenic bacteria and other organisms are also destroyed or inactivated so that the preservative solutions actually purify the milk or other beverage or food.

The germicidal solutions of the present invention may be used very effectively for purifying drinking water and swimming pool water. The same concentrations may be employed as for preserving milk and other beverages. However, much lower concentrations will usually suffice for most water purification applications. The required concentration of the germicidal solution will depend upon the bacteriological contamination that is present or is to be anticipated. The concentrations of the germicidal solution in the water to be treated may be expressed in terms of the parts per million of the iodine to be added. For situations involving a low level of anticipated contamination, approximately 5 parts per million of iodine may be sufficient. For situations involving relatively high levels of contamination, it may be necessary to use iodine concentrations ranging up to 40 to 50 parts per million.

The germicidal solutions of the present invention may be employed very advantageously for purifying sewage effluent, which may be regarded as contaminated water containing dissolved solids and bacterial contamination. Fairly high concentrations of the germicidal solutions will produce effective and longlasting purification. Iodine concentrations ranging up to 50 parts per million or more will be required in most cases.

The germicidal solutions of the present invention may also be employed very advantageously as cleansing and sanitizing agents, particularly as a substitute for hexachlorophene.

The germicidal solutions of the present invention are effective as bacteriocidal agents when applied externally to the human body, but do not have any toxic or other deleterious effect. The iodine-hydrazine hydrate solution is particularly advantageous as a germicidal cleansing agent because it is colorless and virtually odorless.

The germicidal, preservative solutions of this invention can be compounded very easily and inexpensively, by simply mixing operaions, and can be stored for an indefinite period prior to use. The preservative solutions are readily mixable with water, milk and other beverages and foods.

The addition of these preservative solutions to milk makes it possible to keep the milk fresh, sweet and safely drinkable for a long period of time so that the milk can be shipped a long distance. Even if the refrigeration of the milk is inadequate, the milk will keep a long time.

With the use of these preservative solutions, it is possible to store milk when it is abundant and inexpensive, for use when milk is relatively less abundant and more expensive. Other beverages can also be preserved for a long time.

The use of the preservative solutions in milk and other beverages and foods has the beneficial effect of providing enough dietary iodine to prevent goiter and other glandular disturbances which are caused by an iodine deficiency. Thus, the use of the preservative solutions is particularly advantageous in geographical areas where there is a deficiency of iodine in the usual diet.

The preferred germicidal or preservative solution of the present invention consists essentially of hydrazine, which is preferably in the form of hydrazine hydrate, elemental iodine, polyvinyl pyrrolidone, and water for disolving the other constituents, the hydrazine being in a quantity sufficient to cause the iodine to dissolve in the water and to overcome the color of the iodine, so that the solution is substantially colorless. The hydrazine is the sole constituent to cause the iodine to dissolve in the water. The polyvinyl pyrrolidone is preferably used in a quantity sufficient to substantially overcome or neutralize the taste of the iodine and the hydrazine, so that the solution is nearly tasteless.

The hydrazine is a reducing agent and has the effect of stabilizing the solution so that it will remain effective as a germicidal and preservative agent for virtually an indefinite time. In addition, the hydrazine makes it possible to dissolve the elemental iodine in the water, in the necessary quantities to be effective as a germicidal and preservative agent. The hydrazine makes it possible to dispense with the use of an iodide, such as potassium or sodium iodide, which has been used in the prior art to assist in dissolving elemental iodine in water. The elimination of the iodide eliminates the salty taste which the iodide imparts to any solution in which it is used. Furthermore, the hydrazine eliminates the iodine color which would otherwise by present in the solution. The iodides of the prior art do not have the ability to eliminate the iodine color. With the use of the hydrazine, the iodine solution has a high germicidal potentcy. The elimination of any iodide from the solution eliminates the cost of providing any such iodide.

With the inclusion of the hydrazine and PVP, the iodine solution is clear, free from the iodine color, and completely stable. The taste of the solution is very slight and not objectionable. No objectionable taste or color is imparted to beverages or food, when the germicidal solution is employed therein, in small yet effective concentrations. The preparation of the germicidal or preservative solution is simple and easy. The hydrazine makes it easy to dissolve the iodine. No heat is needed to prepare the solution.

The preferred germicidal or preservative solution of the present invention may be modified by omitting the polyvinyl pyrrolidone. The solution then contains only hydrazine, preferably as hydrazine hydrate, elemental iodine and water to dissolve the other constituents. The elimination of the polyvinyl pyrrolidone reduces the cost of the solution and provides an effective germicidal solution which is substantially colorless and highly stable, for use in situations in which the taste of the germicidal solution is not an objectionable factor. The hydrazine is still the sole constituent causing the iodine to be dissolved in the water. The hydrazine also eliminates the color of the iodine in the solution and causes the solution to be highly stable.

I claim:

1. A germicidal solution, consisting essentially of
   hydrazine,
   elemental iodine,
   polyvinyl pyrrolidone,
   and water dissolving the other constituents,
   the hydrazine being in a quantity sufficient to cause the iodine to dissolve in the water and to overcome the color of the iodine,
   said iodine and said polyvinyl pyrrolidone being in approximately the following proportions:
   100 grams of the iodine,
   and 20–100 grams of the polyvinyl pyrrolidone.

2. A germicidal solution, consisting essentially of
   hydrazine,
   elemental iodine,
   polyvinyl pyrrolidone,
   and water dissolving the other constituents,
   the hydrazine being in a quantity sufficient to cause the iodine to dissolve in the water and to overcome the color of the iodine,
   the constituents of said solution being in approximately the following proportions:
   100 grams of the iodine,
   40–60 milliliters of an aqueous solution containing 64% hydrazine hydrate to provide the hydrazine,
   and 20–100 grams of the polyvinyl pyrrolidone.

* * * * *

UNITED STATES PATENT OFFICE
CERTIFICATE OF CORRECTION

Patent No. 4,022,882      Dated May 10, 1977

Inventor(s) Hollis Ely

It is certified that error appears in the above-identified patent and that said Letters Patent are hereby corrected as shown below:

Column 1, line 19, "pathogenci" should be --pathogenic--

Column 1, line 38-39, "solution" should be --solutions--

Column 1, line 46, "apperance" should be --appearance--

Column 3, line 34, after "milk", second occurrence, delete the comma

Column 3, line 61, after "as", second occurrence, "the" should be --ten--

Column 4, line 48, "bases" should be --basis--

Column 4, line 48, after "100", insert --grams--

Signed and Sealed this second Day of August 1977

[SEAL]

Attest:

RUTH C. MASON
*Attesting Officer*

C. MARSHALL DANN
*Commissioner of Patents and Trademarks*